(12) United States Patent
Hamm et al.

(10) Patent No.: US 11,375,881 B2
(45) Date of Patent: Jul. 5, 2022

(54) CATHETER APPARATUS TO CONTROL TORQUE

(71) Applicant: CANON U.S.A., INC., Melville, NY (US)

(72) Inventors: Mark Alan Hamm, Lynnfield, MA (US); Albert Harold Dunfee, Byfield, MA (US); Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 381 days.

(21) Appl. No.: 16/270,304

(22) Filed: Feb. 7, 2019

(65) Prior Publication Data

US 2019/0254506 A1     Aug. 22, 2019

Related U.S. Application Data

(60) Provisional application No. 62/634,011, filed on Feb. 22, 2018.

(51) Int. Cl.
*A61B 1/00* (2006.01)
*A61B 5/00* (2006.01)
(Continued)

(52) U.S. Cl.
CPC ...... *A61B 1/00133* (2013.01); *A61B 1/00045* (2013.01); *A61B 1/00135* (2013.01); *A61B 1/04* (2013.01); *A61B 5/0066* (2013.01); *A61B 5/0084* (2013.01); *A61B 5/6852* (2013.01); *A61B 90/37* (2016.02); *A61M 25/0113* (2013.01); *A61M 25/0136* (2013.01); *A61M 25/0662* (2013.01); *A61B 6/12* (2013.01);
(Continued)

(58) Field of Classification Search
None
See application file for complete search history.

(56) References Cited

U.S. PATENT DOCUMENTS 5,114,403 A     5/1992   Clarke et al.
5,865,800 A     2/1999   Mirarchi et al.
(Continued)

FOREIGN PATENT DOCUMENTS

JP     2007-268133 A     10/2007
JP     2008-194179 A     8/2008
(Continued)

OTHER PUBLICATIONS

Karpiouk, A. B., et al., "Feasibility of in vivo intravascular photoacoustic imaging using integrated ultrasound and photoacoustic imaging catheter", J. Biomed. Opt., Sep. 2012, vol. 17, No. 9.

*Primary Examiner* — John P Leubecker
(74) *Attorney, Agent, or Firm* — Canon U.S.A., Inc., IP Division

(57) ABSTRACT

An apparatus includes an elongate member having proximal and distal portions; a rotatable drive cable disposed within the elongate member, the drive cable being connectable to a mechanism to which torque can be applied; and a control assembly mechanically coupled to the drive cable, and configured to disengage the mechanism from the drive cable when the applied torque exceeds a predetermined level, wherein disengagement of the mechanism from the drive cable causes rotation of the drive cable to stop or withdrawal of the drive cable.

18 Claims, 14 Drawing Sheets

(51) Int. Cl.
*A61B 90/00* (2016.01)
*A61B 1/04* (2006.01)
*A61M 25/01* (2006.01)
*A61M 25/06* (2006.01)
*A61B 6/00* (2006.01)
*A61B 6/12* (2006.01)
*A61B 8/12* (2006.01)

(52) U.S. Cl.
CPC ............ *A61B 6/4441* (2013.01); *A61B 6/487* (2013.01); *A61B 8/12* (2013.01); *A61B 2090/031* (2016.02); *A61B 2090/037* (2016.02); *A61B 2090/066* (2016.02); *A61M 2205/332* (2013.01)

(56) References Cited

U.S. PATENT DOCUMENTS

| | | |
|---|---|---|
| 6,454,717 B1 | 9/2002 | Pantages et al. |
| 6,517,528 B1 | 2/2003 | Pantages |
| 6,758,818 B2 | 7/2004 | Pantages et al. |
| 8,317,791 B2 | 11/2012 | Phan |
| 8,323,203 B2 | 12/2012 | Thornton |
| 8,388,565 B2 | 3/2013 | Shifflette |
| 8,926,590 B2 | 1/2015 | Petroff |
| 9,039,626 B2 | 5/2015 | Courtney |
| 9,220,529 B2 | 12/2015 | Rivers et al. |
| 9,360,630 B2 * | 6/2016 | Jenner .................. G02B 6/3604 |
| 9,622,706 B2 * | 4/2017 | Dick .................... A61B 5/6852 |
| 10,792,012 B2 * | 10/2020 | Hutchins ............. A61B 5/0084 |
| 2002/0151799 A1 | 10/2002 | Pantages et al. |
| 2007/0232893 A1 | 10/2007 | Tanioka |
| 2009/0247878 A1 * | 10/2009 | Tanioka ............... A61B 5/0084 600/462 |
| 2011/0151980 A1 | 6/2011 | Petroff |
| 2013/0023761 A1 | 1/2013 | Petroff |
| 2015/0209072 A1 | 7/2015 | Higgins et al. |
| 2016/0000406 A1 * | 1/2016 | Petroff ................ A61B 5/0066 600/425 |

FOREIGN PATENT DOCUMENTS

| | | |
|---|---|---|
| JP | 2009-240710 A | 10/2009 |
| JP | 2016-087242 A | 5/2016 |
| WO | 2016168605 A1 | 5/2015 |

\* cited by examiner

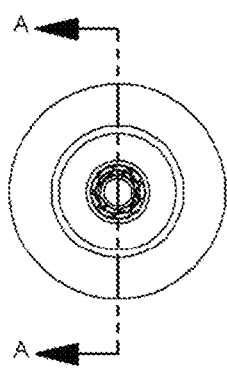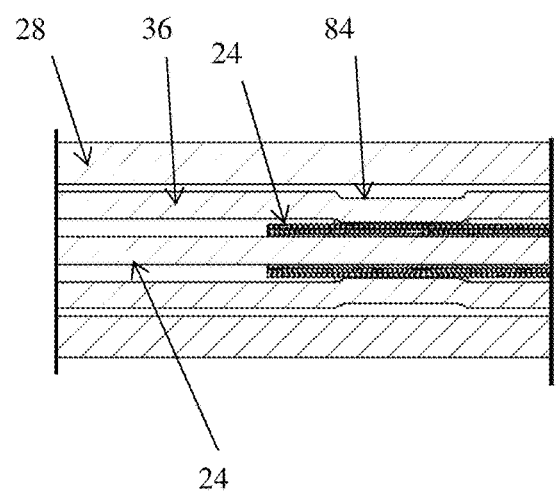
FIG. 9A
FIG. 9B

CATHETER APPARATUS TO CONTROL TORQUE

CROSS-REFERENCE TO RELATED APPLICATIONS

This application claims priority to U.S. Provisional Application Ser. No. 62/634,011 filed Feb. 22, 2018, the contents of which is herein incorporated by reference in its entirety.

BACKGROUND

Field of the Disclosure

The present disclosure generally relates to medical devices and, more particularly, to an apparatus, a method, and a system to sense or affect torque.

Description of the Related Art

Medical devices, such as catheters, visualization devices or the like, are known for accessing a body cavity and directing passage of devices into the cavity. A catheter is an example of such a medical device, and may generally include a flexible or rigid hollow tube that passes through the body to provide imaging, diagnosis, and treatment of tissues, and may be used, for example, to perform radial scanning within a blood vessel, to receive a reflected wave(s) (ultrasound echoes) reflected by bio-tissue (e.g. the blood vessel wall), or the like.

Catheters may be inserted in a body area such as a blood vessel, a ureter, a bronchus, an alimentary canal, a lymph vessel, or the like. Medical treatments or minimally invasive procedures that use catheters may include, for example, preventing rupture of a cerebral aneurysm by guiding a tip end of a catheter representing a hollow tube to a mouth of the cerebral aneurysm through a blood vessel from outside the body, thereafter inserting an embolization coil and a delivery wire representing linear bodies having flexibility in the catheter, and filling the cerebral aneurysm with the embolization coil if available. If excess load is applied to the cerebral aneurysm by the embolization coil and the delivery wire, however, the cerebral aneurysm may be damaged.

A catheter may be passed through one or more body lumens to access a target location within the human body. The catheter may be inserted into an artery or vein through a relatively small incision in the patient's body. The catheter is then threaded through the patient's system of blood vessels to reach the desired target area. Such medical devices may include various other components, for example, surgical instruments, lasers, electronic devices, imaging devices, fiber optic cables, sensors capable of monitoring various physiological parameters, or the like. Catheters are commonly used as medical devices that are inserted in a vessel in a body such as a blood vessel, a ureter, a bronchus, an alimentary canal, a lymph vessel, or the like.

Rotating element catheters may be used to provide a diagnostic or therapeutic effect within the body tissue of a patient, e.g., ultrasonic or optical tomographic imaging or artherectomy. A typical rotating element catheter may include a flexible drive cable that extends the length of the catheter body, connecting to a torque applicator, such as a motor drive unit or the like. The flexible drive shaft is normally coupled to the motor, and the motor normally drives the drive cable at a fixed rotational rate from the proximal end of the catheter body. The instantaneous rotational rate of the distal end of the drive cable at the distal end of the catheter body may differ from and not be the same as the fixed rotational rate at the proximal end. An operative element, e.g., an ultrasonic transducer, an artherectomy blade, or the like, may be distally mounted to the drive cable. Operation of the drive unit rotates the drive cable, which, in turn, rotates the operative element at high speeds or rpms (revolutions per minute) to produce the desired diagnostic or therapeutic effect. Due to the nature of placing indiscriminately rotating elements inside a patient, although the anatomy is protected from the rotating element by a stationary catheter sheath, there is always a risk that the rotating element could inadvertently damage tissue if the catheter is damaged, defective or mishandled.

For example, some imaging catheters can provide two or three dimensional images along the length of a blood vessel by rotating a transducer at high speeds, while linearly moving the transducer in a proximal direction relative to the user. If the distal end of the catheter becomes prolapsed or kinked, or otherwise forms into a tight curve, the rotating element may be trapped or pinched, causing an increase in torque, or may inadvertently pass through the catheter wall and cause damage to or rupture surrounding tissue. This may be caused by the drive unit of the transducer of the catheter operating at a set speed, whereby the torque applied to the drive cable may increase or decrease as a result of the above complication(s). As a result, abnormal frictional loads between the drive cable and the catheter may occur and cause the rotating element to pierce the wall of the catheter and possibly damage or alter the body tissue.

Catheters with rotating drive cables can implement mechanisms to reduce excess torque of the drive cables that could cause damage to the catheter sheath and/or cause harm to the patient. For example, some catheters include sacrificial components that are intended to break at pre-determined torques. The sacrificial components that connect the motor drive to rotating elements that extend within the anatomy may be fitted with a weak portion that will break if excess torque occurs from the catheter sheath, or is applied to the rotating element, e.g. during entanglement, prolapse, or other complication that compromises the integrity of the sheath, or which may cause clamping or pinching of the rotating imaging core.

Methods of limiting torque and torque limiters have been described, for example, by U.S. U.S. Pat. Nos. 6,758,818; 6,454,717; 6,517,528; and 9,220,529, and U.S. Pat. Pub. 2007/0232893. However, there is still need for safe, useful, and innovative apparatus and method for sensing and/or affecting the torque within a catheter system, such as by limiting the torque.

SUMMARY

According to one or more aspects of the present disclosure, an apparatus includes an elongate member having proximal and distal portions; a rotatable drive cable disposed within the elongate member, the drive cable being connectable to a mechanism to which torque can be applied; and a control assembly mechanically coupled to the drive cable, and configured to disengage the mechanism from the drive cable when the applied torque exceeds a predetermined level, wherein disengagement of the mechanism from the drive cable causes rotation of the drive cable to stop or withdrawal of the drive cable In other embodiments, there is provided a system comprising the apparatus as described herein and methods of use thereof.

According to some aspects of the present invention, the drive cable is axially translatable in proximal and distal directions. According to some aspects of the invention, the predetermined level at which there is a disengagement of the mechanism from the drive cable is when shear failure occurs.

Thus, in some aspects of the invention, the elongate member is a sheath, and disengagement of the mechanism from the drive cable is based on at least one of a low-shear adhesive, a broken optical fiber, slippage of a mechanical crimp of a hypotube onto the drive cable, an unsupported segment of the drive cable, and a driving dog structure. In some embodiments, the disengagement may be based on two or more of a low-shear adhesive, a broken optical fiber, slippage of a mechanical crimp of a hypotube onto the drive cable, an unsupported segment of the drive cable, and a driving dog structure. To perform well with respect to Non-Uniform Rotation Distortion, or NURD, the drive cable requires the support of a tube with minimal clearance between the drive cable outer diameter and the sheath inner diameter.

In some aspects of the invention, the apparatus also comprising a short linear segment where the drive cable passes through an unsupported gap within a predetermined length range so the drive cable can wind up in the unsupported gap and be withdrawn from a site of complication or entanglement. The apparatus may also comprise a catheter sheath disposed around the drive cable, where the catheter sheath may comprise a hypotube disposed about the drive cable and a handle disposed about the hypotube, where the hypotube is preferably adhesively bonded to an optical fiber, the optical fiber is bonded to the drive cable, and there is no direct bond between the drive cable and the hypotube.

In an exemplary embodiment, the unsupported gap has a length in a range between around two and twenty times the drive cable diameter. In another exemplary embodiment, the unsupported gap has a diameter in a range between around three and twenty times the drive cable diameter.

The mechanism may be mounted on a drive shaft, and the drive shaft is interconnected with a motor drive unit. In some embodiment, the drive cable is connected at a distal portion of the hypotube with adhesive. A torque sensor configured to detect applied torque may also be included as part of the apparatus.

For yet other aspects of the invention, a method is provided, the method comprising: inserting, into a subject, an elongate member having proximal and distal portions, and a rotatable drive cable disposed within the elongate member, the drive cable being connected to a mechanism to which applies torque, and being mechanically coupled to a control assembly; and applying torque to the drive cable member, wherein the mechanism will disengage from the drive cable when the applied torque exceeds a predetermined level, and wherein disengagement of the mechanism from the drive cable causes rotation of the drive cable to stop or withdrawal of the drive cable. The torque applied to the apparatus may be detected with a torque sensor, particularly when sheath complications occur that could increase said torque, where the sensor is capable of detecting said increase in said torque, and quickly turning off the motor.

According to some aspects of the present invention, a system is provided, where the system is, for example, an OCT system, which comprises: an imaging device; a display; a controller; and an apparatus, the apparatus comprising: an elongate member having proximal and distal portions; a rotatable drive cable disposed within the elongate member, the drive cable being connectable to a mechanism which applies torque; and a control assembly mechanically coupled to the drive cable, and configured to disengage the mechanism from the drive cable when the applied torque exceeds a predetermined level, wherein disengagement of the mechanism from the drive cable causes rotation of the drive cable to stop or withdrawal of the drive cable. Each of the aspects of the invention discussed for the apparatus may also be included on the apparatus of the system as described herein. The system may also comprise one or more of a rotary junction, a detector, and a light source.

Further features of the present disclosure will become apparent from the following description of exemplary embodiments with reference to the attached drawings.

BRIEF DESCRIPTION OF THE DRAWINGS

FIG. 9(A) illustrates a cross sectional view of an apparatus according to one or more aspects of the present disclosure. FIG. 9(B) illustrates a portion of the apparatus according to FIG. 9(A).

FIG. to illustrates a cross-sectional view of a portion of the apparatus according to one or more aspects of the present disclosure.

Figure 11:
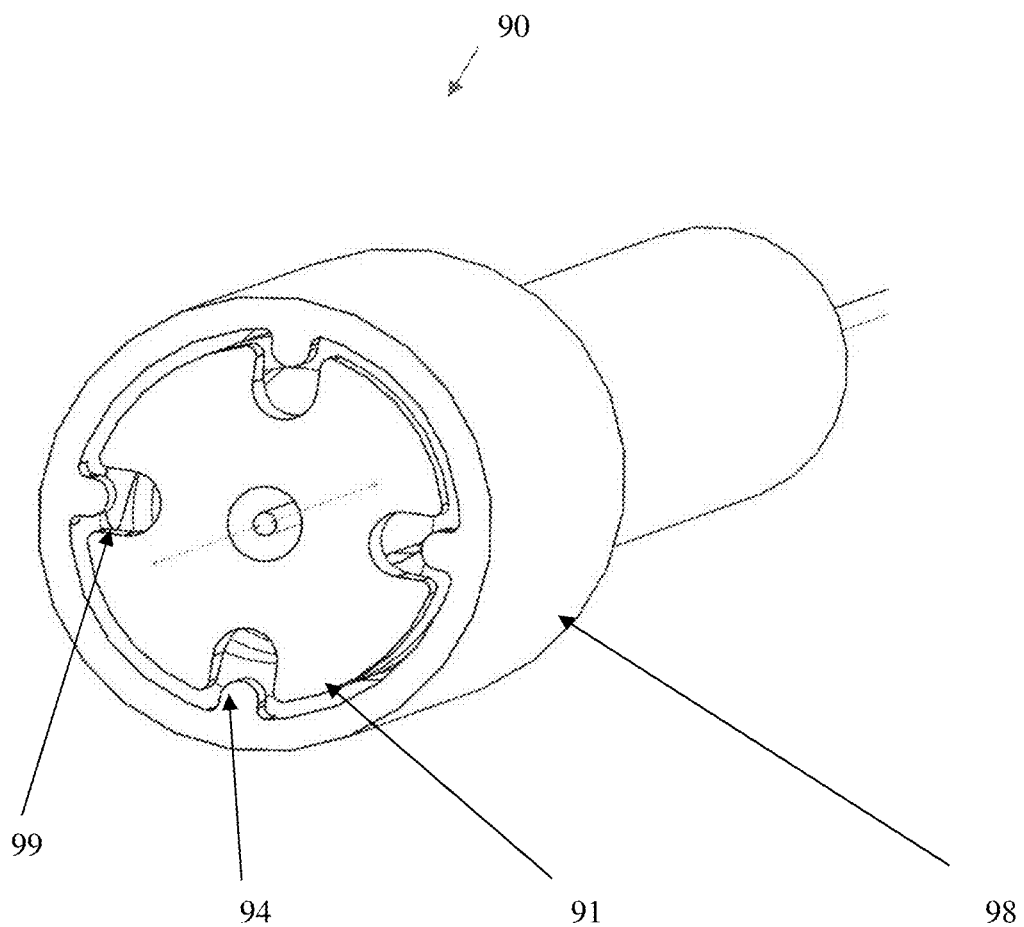

FIG. 11 illustrates a cross-sectional view of a portion of the apparatus according to one or more aspects of the present disclosure.

Figure 12:
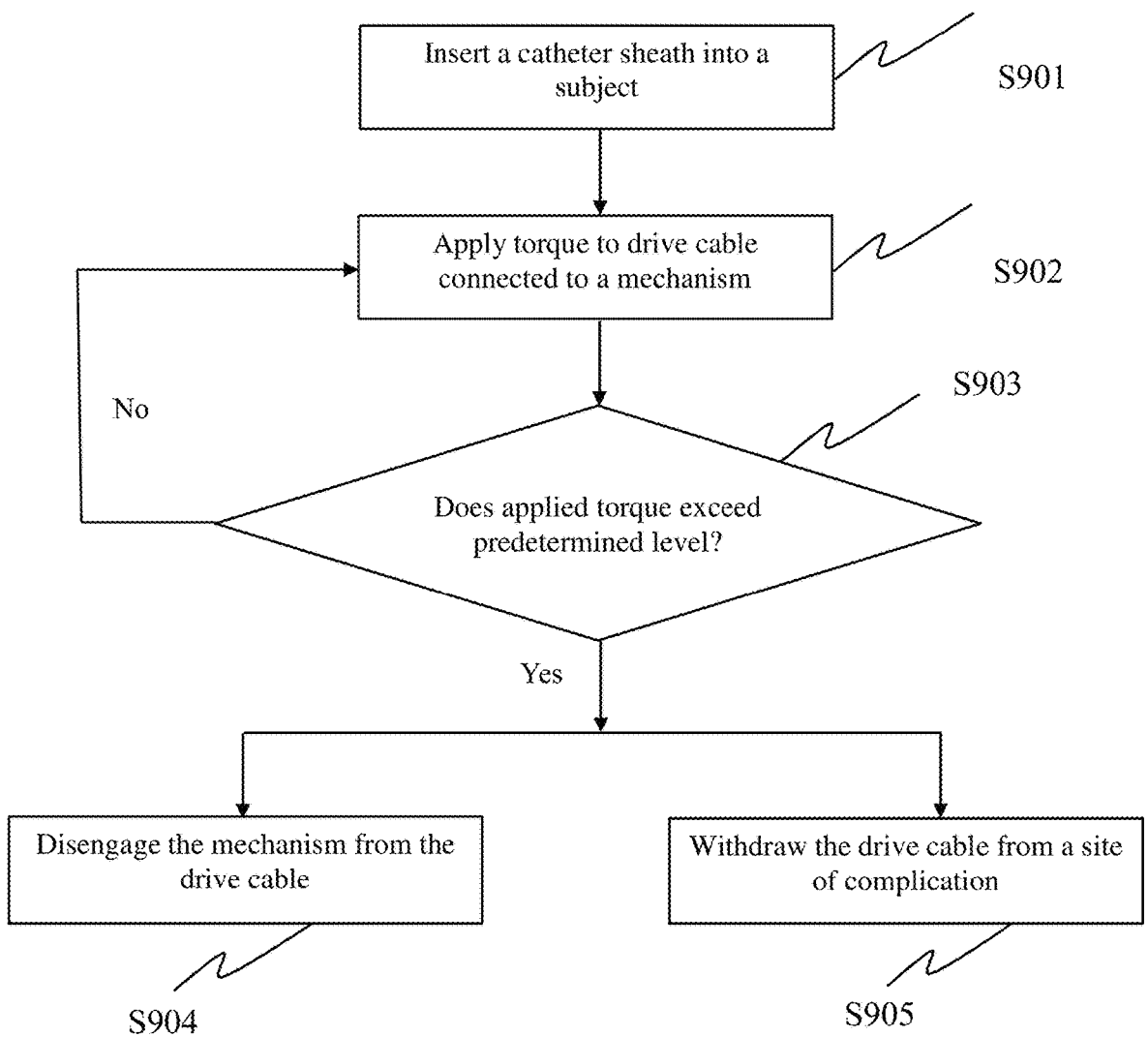

FIG. 12 is a flowchart according to one or more aspects of the present disclosure.

Figure 13:
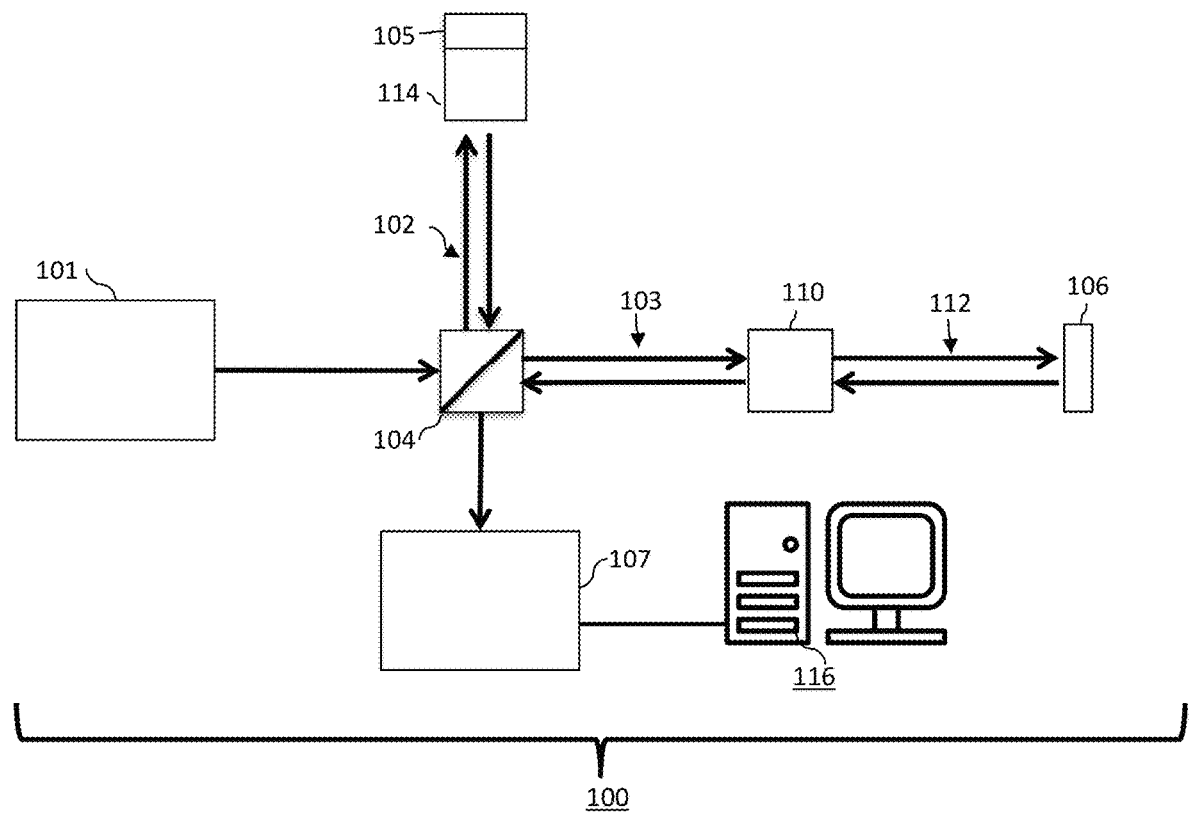

FIG. 13 illustrates an exemplary system using the apparatus according to one or more aspects of the present disclosure.

DESCRIPTION OF THE EMBODIMENTS

Various exemplary embodiments, features, and aspects of the present disclosure will be described in detail below with reference to the accompanying drawings. The following exemplary embodiments do not limit the present disclosure to the scope of the appended claims. Not all of the combinations of the features described in the present exemplary embodiments are indispensable to the solutions of the present disclosure. The same reference numerals are assigned to identical components, and duplicated descriptions thereof will be omitted.

Figure 1:
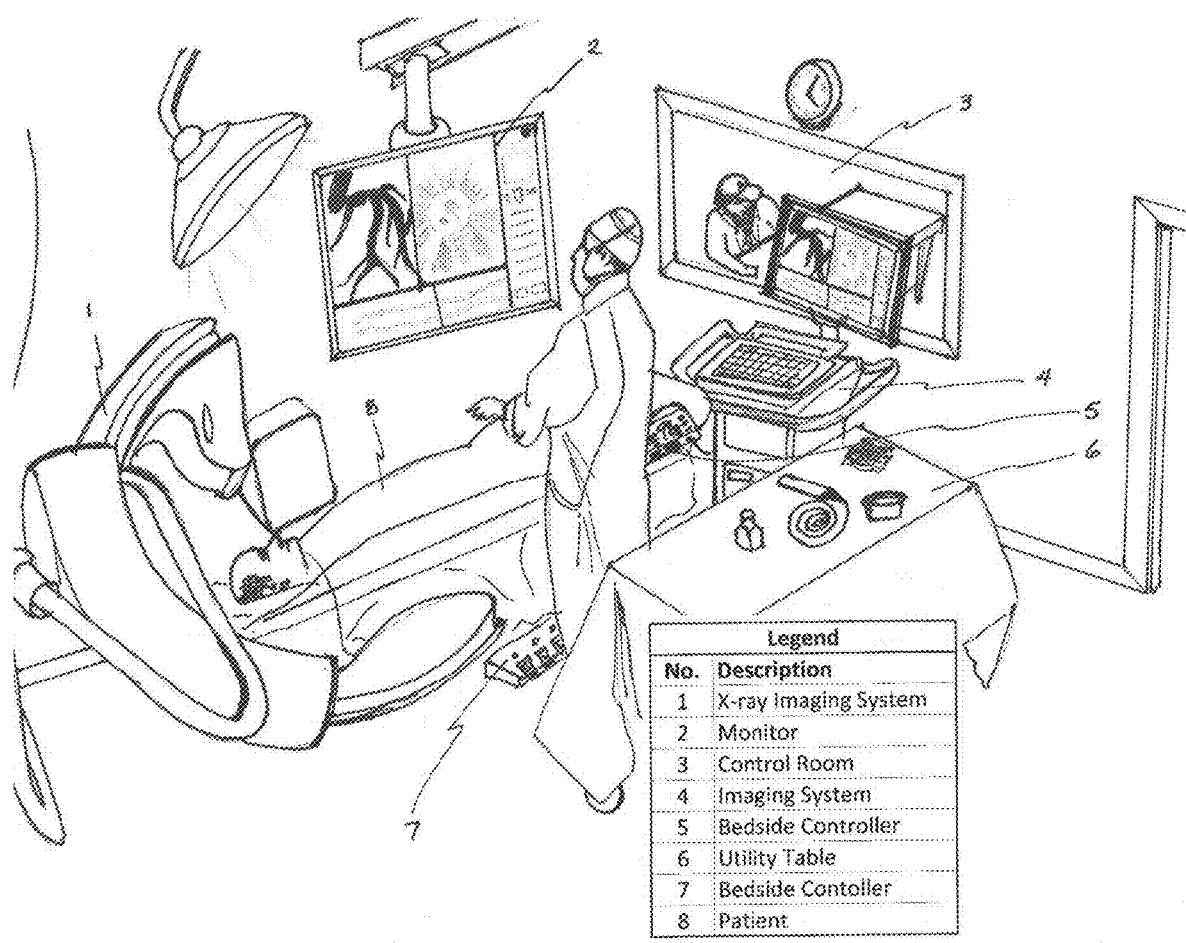
FIG. 1 illustrates an environmental view of a system according to one or more aspects of the present disclosure.

FIG. 1 illustrates a system according to one or more aspects of the present disclosure. The system is generally shown in an environment that may be associated with a medical procedure, for example, an orthopedic procedure, a neural procedure, a spinal procedure, or the like. It is to be understood, however, that the system may be associated with other types of operating environments and objects, such as non-medical environments, mechanical objects, etc.

The system of FIG. 1 may include an imaging device 1, a display 2, a control room 3, a cart-based imaging system 4, a controller 5, a table 6, a foot-switch controller 7, and a medical object 8. The device 1 may be, for example, a two-dimensional (2D), three-dimensional (3D), four-dimensional (4D) imaging device, or the like, such as a fluoroscope x-ray imaging device that may be configured as a C-arm having an x-ray source and an x-ray receiving section. Other imaging devices may be used, such as isocentric fluoroscopy, bi-plane fluoroscopy, ultrasound, computed tomography (CT), multi-slice computed tomography (MSCT), optical coherence tomography (OCT), intra-vascular ultrasound (IVUS), single photo emission computed tomography (SPECT), or the like. Other types of fluoroscopic systems may be used, for example, ceiling fluoroscopic systems, cath-lab fluoroscopic systems, bi-plane fluoroscopic systems, isocentric C-arm fluoroscopic systems, three-dimensional (3D) fluoroscopic systems, or the like. Image data may be obtained with other types of imaging devices and various imaging or radiation sensors may be provided. The image data may undergo one or more image processing procedures. The display 2 may display one or more images generated based on the image data, and may be a liquid crystal display (LCD), a cathode ray tube (CRT) display, a light emitting diode (LED) display, or the like.

The control room 3 may include various devices to control elements in the system. The cart 4 may be an OCT system cart or the like. The controller 5 may be a bedside controller or the like. The table 6 may be a utility table or the like. The controller 7 may be C-arm controller or the like. The object 8 may be a medical object, such as a patient or the like.

The control room 3, the controller 5, and/or the controller 7, for example, may include a central processing unit (CPU), a read-only memory (ROM), a random access memory (RAM), an external storage apparatus. These devices may be mutually connected via a system bus. The CPU, which may include one or more processors and one or more memories, controls the operation of the devices. The CPU performs various processes described below by reading a program stored on the ROM onto the RAM and executing the program. The ROM is a read-only memory so that, for example, a system boot program, a program for controlling the devices, instructions for controlling the devices, or the like, are stored on the ROM. The RAM is a volatile random access memory and used as a work area of the CPU, and a temporal storage area for various data. For example, the RAM is used as a storage area, for example, for storing the image data, or other data received from an external device. The external device may include, for example, a hard disk to store various data, and may be used as a storage area or a work area for a program, instructions, an information file, image data, etc. The one or more memories may include programs, instructions, codes, or the like, for performing the one or more image processing procedures, and the one or more processors may execute the one or more image processing procedures based on the instructions.

The units described throughout the present disclosure are exemplary and/or preferable modules for implementing processes described in the present disclosure. The modules can be hardware units (such as circuitry, a field programmable gate array, a digital signal processor, an application specific integrated circuit, or the like) and/or software modules (such as a computer readable program or the like). The modules for implementing the various steps are not described exhaustively above. However, where there is a step of performing a certain process, there may be a corresponding functional module or unit (implemented by hardware and/or software) for implementing the same process. Technical solutions by all combinations of steps described and units corresponding to these steps are included in the present disclosure.

One or more aspects of the present application relate to an apparatus that includes an elongate member having a proximal portion and a distal portion. The apparatus may be a tubular device, such as a catheter or lumen. A rotatable drive cable may be disposed within the elongate member. The drive cable may be interconnected with a torque applicator to which torque can be applied. A torque sensor or transducer may be configured to detect applied torque. In some aspects, the torque sensor may have a rotational rate sensor. A control assembly may be mechanically coupled to the drive cable, and may be configured to disengage the torque applicator from the drive cable when the applied torque exceeds a predetermined level, or if the imaging core cannot advance due to a compromised sheath. Alternately, the system may reduce and/or eliminate the danger of piercing through the wall of the tubular member (catheter sheath) by other means, such as quickly withdrawing the rotating member when applied torque above a predetermined level is encountered.

The elongate member may be a tubular device, such as a catheter sheath 22 or lumen. Suitable materials for medical use may include, for example, PTFE (polytetrafluoroethylene), PEEK (polyetheretherketone), polyamides, polyurethanes, polyesters, polyvinylchloride, fluoropolymers, polyethylene terephthalate, polyethylene, silicon, silicone rubbers, natural rubbers, organic polymers, combinations thereof, or the like. The elongate member may include one or more lumens which terminate at the distal portion in a configurational shape, such as cylindrical or the like, to facilitate passage into a body cavity. The cross-sectional shapes of the lumens may vary along their lengths, e.g. circular, oval, asymmetrical, or the like, and the outer surface of the lumens may be lubricated to help them slide relative to each other. Similarly, the outer surface of the catheter sheath has a low friction coating to enhance navigation and guidewire tracking properties.

A rotatable drive cable may be disposed within the elongate member and be interconnected with a drive shaft that is driven by a motor drive unit or the like. The rotatable drive cable may be coupled to the motor, and the motor drive unit may drive the drive cable at a fixed rotational rate near the proximal portion of the elongate member. The instantaneous rotational rate of the drive cable at the distal portion of the elongate body may differ from and not be the same as the fixed, average rotational rate near the proximal end. Measurement of the rotatory torque of the motor drive unit and/or the rotatable drive cable may be obtained using one or more torque sensors.

One or more sensors or transducers may be in the elongate member to obtain data and/or sense aspects from within and outside of the elongate member, and one or more torque sensors or transducers may be provided to sense the tension or torque of the drive cable. Electrical current corrections by a motor servo or a control computer may be used to reduce or eliminate an error between any difference between an actual and a commanded motor torque value. Examples of such sensors or transducers may include various components, such as image sensors, pressure sensors, temperature sensors, force sensors, torque sensors, velocity sensors, acceleration sensors, position sensors, proximity sensors, motion sensors, location sensors, load sensors, ultrasonic range sensors, infrared sensors, object sensors, optical fibers, ultrasound transducers, rotary encoders, optical encoders, magnetic encoders, resistive encoders, reflectors, mirrors, prisms, conductors, cameras, lenses and/or combinations thereof, for diagnostically assessing a target region of an object, e.g. a patient. One or more conductors may be configured to carry signals representing information captured by each transducer to a controller. Electrical signal connection between the distal and proximal portions of the elongate member may be provided by wiring, for example, as one or more pairs of elongate, insulated metal cores extending through the elongate member. A holding device, such as a handle or the like, may be attached to the proximal portion of the elongate member for holding and manipulating and/or connecting the elongate member to the drive shaft.

The drive cable may flexibly extend to the distal portion of the apparatus and be sized to fit within the elongate member. The drive cable may preferably be rotatable, axially translatable in proximal and distal directions, may have flexural stiffness and torsional rigidity to transmit torque to the distal portion of the elongate member, and may be configured with counter-wound helical coils. The coils may be wound in opposite directions so that when the cable body is rotated, one of the coils will tend to tighten, providing a very high torsional modulus of elasticity while reducing the flexural modulus of elasticity due to the nature of the coil structures. The drive cable may alternatively be configured as braided fibers, braided metals, co-extruded polymers over braided structures, a hypotube, or the like. The drive cable may transmit a drive force from the motor drive unit interconnected at the proximal portion of the elongate member to the distal portion of the elongate member. The drive cable may be configured to provide desirable levels of torque and speed that may vary in the level of torque to the level of speed, for example high speed/low torque, low speed/high torque, or variations thereof. The drive force may be provided by the motor drive unit using gearing arrangements at the distal and/or proximal portions of the drive cable. Such gearing arrangements may be configured to convert, for example, high speed/low torque to low speed/high torque or variations thereof. The drive cable may be axially translatable in proximal and distal directions, flexible and has a length sufficient to extend beyond the proximal portion of the elongate member and near the distal portion of the elongate member. The rotary motion of the drive cable and the motor drive unit may be measured or estimated through use of one or more torque sensors. The output of the torque sensors may provide input to a controller to control the speed of the motor drive unit and the proximal end of the drive cable. The drive cable may have constant flexibility over the entire length of the drive cable, or may have one or more sections having different flexibilities based on mechanical properties. Factors influencing the elastic properties of the drive cable and the catheter may include but are not limited to elasticity of the materials used, the length, and the thickness of the walls. The drive cable may preferably be able to laterally bend, has sufficient torsional stiffness to minimize rotational wind up, and sufficient flexural stiffness to avoid seizing and binding of the drive cable. In some embodiments, the elongate member may be a sheath, and disengagement of the mechanism from the drive cable may be based on at least one of low-shear adhesive, broken optical fiber, slippage of the mechanical crimp of hypotube onto drive cable, an unsupported segment of the drive cable, and a driving dog structure.

Distinguishable configurational elements of one or more aspects of the present disclosure minimizes risk of harm and provides additional failsafe and a layer of protection against the risk of harm to the patient, by causing rotation of the drive cable to stop or withdrawal of the drive cable based on sensing of excess torque and/or motor shut-off, or if the imaging core cannot advance due to a compromised sheath, or by causing shear failure in the event of torques encountered that are higher than a predetermined level.

Figure 2A:
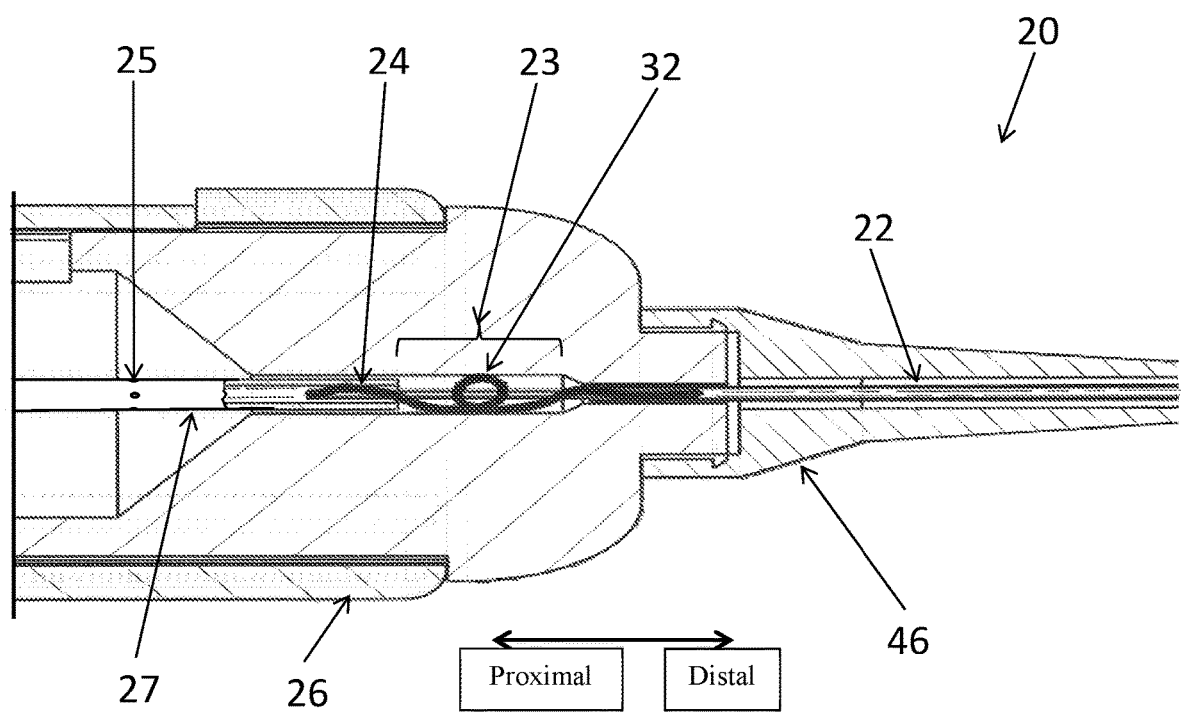
FIG. 2(A) illustrates a portion of an apparatus according to one or more aspects of the present disclosure.
Figure 2B:
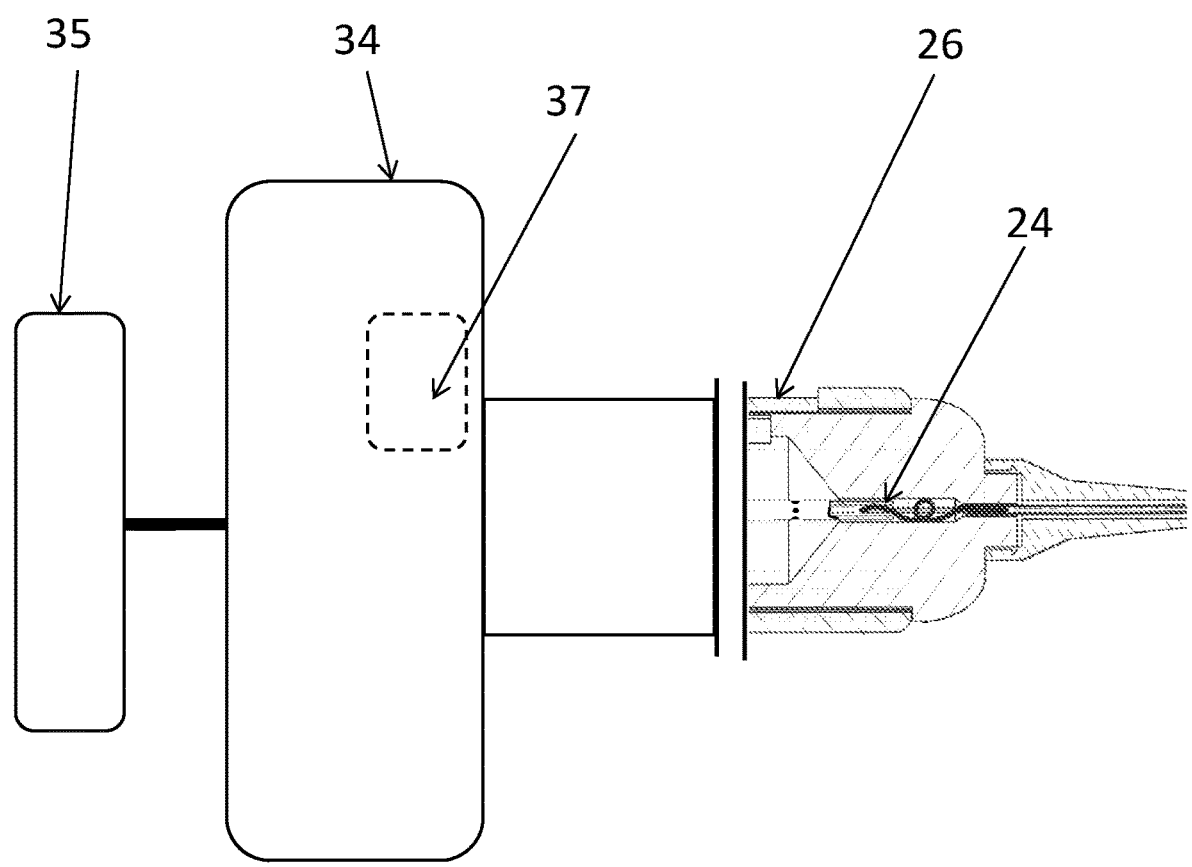
FIG. 2(B) illustrates a power source and motor drive unit portion of an apparatus according to one or more aspects of the present disclosure, and containing the portion shown in FIG. 2(A).

FIG. 2(A) illustrates a cross-section of an apparatus 20 according to one or more aspects of the present disclosure. The apparatus 20 may be a catheter and includes a catheter sheath 22 having a proximal portion and a distal portion. A rotatable drive cable 24 may be disposed within catheter sheath 22. As shown in FIG., 2(B), the drive cable 24 may be connectable to a mechanism 34 which applies torque. The apparatus may include a torque sensor 37 configured to detect applied torque. In this embodiment, the torque sensor 37 is located in the motor. However, in other embodiments, the torque sensor 37 may be located, for example, in the handle or in the catheter. A control assembly may be mechanically coupled to the drive cable, and may be configured to disengage the mechanism from the drive cable when the applied torque exceeds a predetermined level, or if the imaging core cannot advance due to a compromised sheath. Crimp 25 is one preferred way to mechanically connect drive cable 24 to the mechanism 34. Crimp 25 can only transmit a limited torque to drive cable 24, above which the connection slips or is parted. When the torque exceeds a pre-determined limit, crimp 25 slips with respect to the drive cable 24 and can pull out of hypotube 27, which transfers torque to drive cable 24. As illustrated, a handle 26 may be attached to a proximal portion of the catheter 20 for users to handle the catheter 20. Drive torque typically ranges between around 0.01 mN-m (milli Newton meter) and 0.50 mN-m under normal operating conditions in coronary blood vessels.

The drive cable 24 may be flexible laterally and torsionally rigid such that it transmits rotary motion and angular rotation to the distal portion where distal transducers, such as optics or the like, scan the anatomy. The flexible drive cable can be supported in the sheath or tube in a close-fitting manner to accurately transmit the rotary motion and angular acceleration. If the drive cable 24 is not properly supported by the sheath 22 or Teflon tube 28, the drive cable may possibly wind up within an unsupported segment 23 and withdraw the rotating, imaging core assembly away from the patient and/or area that has been compromised, such as entanglement, pinch, kink, prolapse, or the like. The drive cable 24 may be coupled to a hypotube, which may be interconnected with a drive assembly 34 including, for example, a motor drive unit. A torque sensor or transducer 37 may be provided that may be configured to detect applied torque. The motor drive unit may provide rotation to a drive shaft and/or an optical fiber of a catheter, and may provide axial translation of the drive shaft and/or the optical fiber of the catheter. A power source 35 may be connected to the drive assembly to provide driving power. As the motor drive unit turns, the drive cable rotates, thereby conveying motor torque throughout the length of the apparatus. A control assembly may be mechanically coupled to the drive cable, and may be configured to disengage the mechanism from the drive cable when the applied torque exceeds a predetermined level, or if the imaging core cannot advance due to a compromised sheath. The drive cable may be configured to transmit torque at a high rpm by adjusting various characteristics of the drive cable, such as tension, length, bending stiffness, torsional stiffness and linear mass density. It may be desirable to maintain a ratio of bending rigidity to torsional rigidity within a range of around 0.005 to 0.035 to achieve high quality image fidelity and this torque control.

In a case where the torque sensor detects applied torque that exceeds a predetermined level, or if the imaging core cannot advance due to a compromised sheath, the motor drive unit may shut off. In combination with shut off of the motor drive unit, the catheter handle may be configured to provide an additional safety system by taking advantage of the drive cable configuration by providing a short linear segment where the drive cable is not supported by a close-fitting inner diameter, for example, by leaving an unsupported gap 23 within a predetermined length range, for example, preferably between around 1 mm and 25 mm at a diameter that may be in a range between around two or three and twenty times the diameter of the drive cable itself. The unsupported gap can be located in the handle 26, or alternately in the strain relief 46. This area may be located outside the body, in this case in the catheter handle/connector so that drive cable breakage or jamming at the location in response to complications within the body will do no harm to the patient or user. While dimensions of the unsupported gap 23 may vary, the dimensions of the unsupported gap may preferably have a length in a range between around two and twenty times the drive cable diameter, and the diameter may preferably be between around two or three and twenty times the drive cable diameter.

This configuration of the catheter may include a drive cable contained within a catheter handle/connector, where strain relief may be provided for the catheter sheath. In the catheter handle/connector, an unsupported gap length may be provided so that, after excess torque is applied, the drive cable can wind up, creating a knot 32 in the unsupported gap 23 and cause rotation of the drive cable to stop, or alternatively, cause withdrawal of the drive cable away from the obstruction or other source of excess torque. The combination of two different safety systems working in tandem may adequately address and mitigate the risk of harm via drill-through, perforation, dissection, or the like. Distinguishable configurational elements of this configuration of the drive cable minimizes risk of harm and provides additional fail-safe and a layer of protection against the risk of harm to the patient, by causing rotation of the drive cable to stop or alternatively, causing withdrawal of the drive cable away from the obstruction or other source of excess torque, and also causing the motor to shut off based on sensing of excess torque or inability of the core to advance back to the start position after an imaging pullback.

Figure 3:
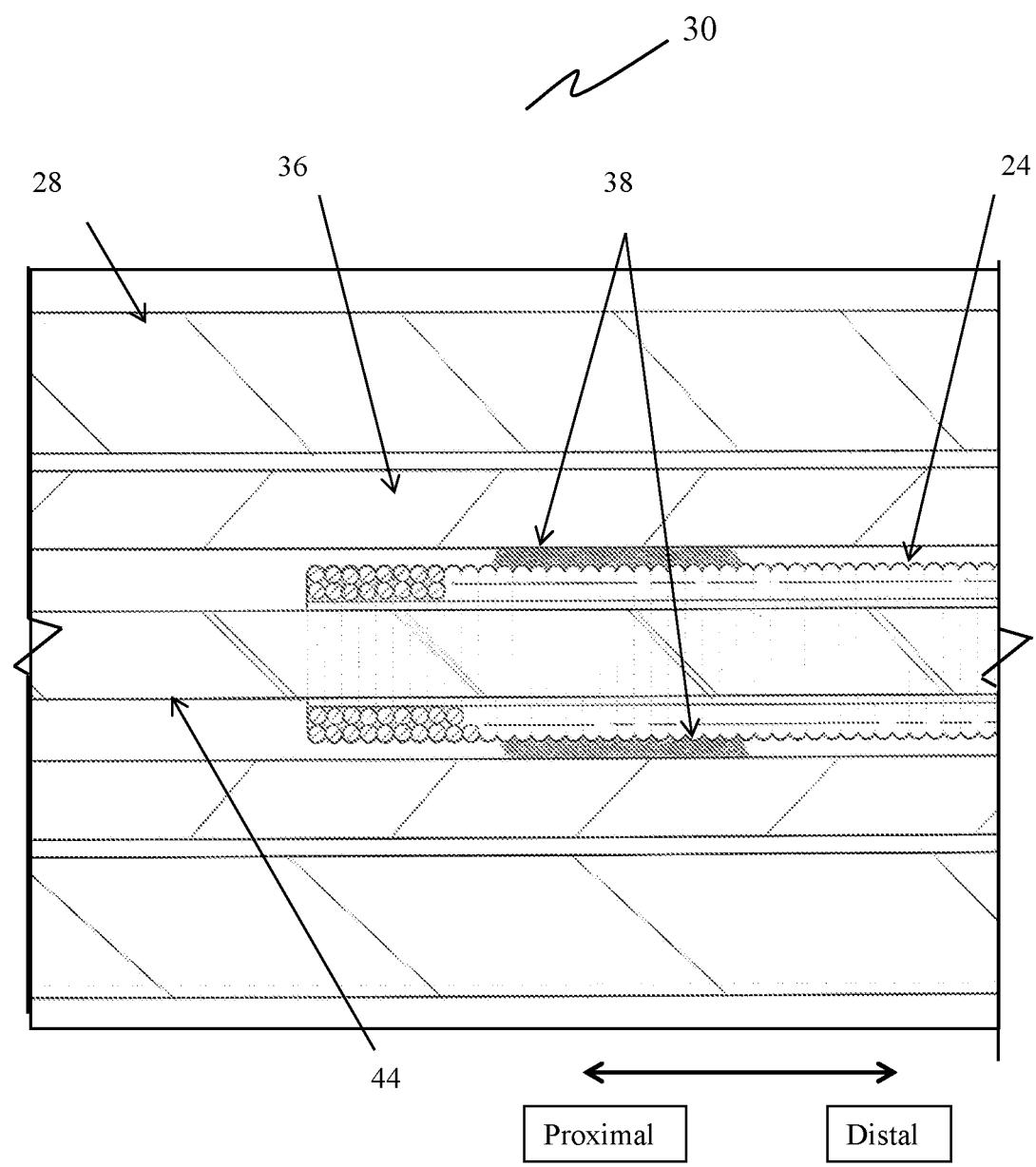
FIG. 3 illustrates a portion of an apparatus according to one or more aspects of the present disclosure.

FIG. 3 illustrates a side view cross-sectional image of an apparatus 30 according to one or more aspects of the present disclosure. The apparatus 30 may be a catheter and includes an elongate member having a proximal portion and a distal portion. The elongate member of the catheter 30 may comprise a catheter sheath assembly 22 (not shown) disposed about a rotatable drive cable 24 in a telescoping assembly. A hypotube 36 may be disposed about a portion of the drive cable 24. A tube 28, which may be Teflon, PTFE, or the like, may be disposed about the hypotube 36. The drive cable 24 is disposed within the tube 28. The hypotube 36 may be bonded to the drive shaft 24 by a low-shear adhesive 38. Preferably, other than the low-shear adhesive, there is no direct bond between the drive cable 24 and the hypotube 36. The low-shear adhesive 38 preferably breaks via shear failure in the event of torque encountered within the catheter 30 that are higher than a predetermined level. The low-shear adhesive 38 may be weak glue, rubber cement, low-shear strength ultraviolet curable adhesive, or the like, provided that the shear force is low enough to be effective as a torque limiter failsafe mechanism to prevent harm occurring to the patient or user.

The low-shear adhesive or optical fiber 44 may be used to bond directly between the drive cable 24 and hypotube 36, thus using a very low shear strength adhesive that will shear, thus quickly and effectively disconnecting the drive cable 24 from the motor drive unit and stopping rotation. Adhesives may be used to 'indirectly' bond the drive cable to the hypotube 36, e.g., bonding optical fiber 44 to drive cable 24 and also bonding the optical fiber 44 to the hypotube 36 with no direct bond between drive cable 24 and hypotube 36, so any normal epoxy may be used for this application. In this way, the shear strength of the optical fiber may be used so no harm will come to a patient via scenarios involving catheter entanglement, kinking, pinching, prolapse, or the like, even in the event of a catheter failure.

Figure 4:
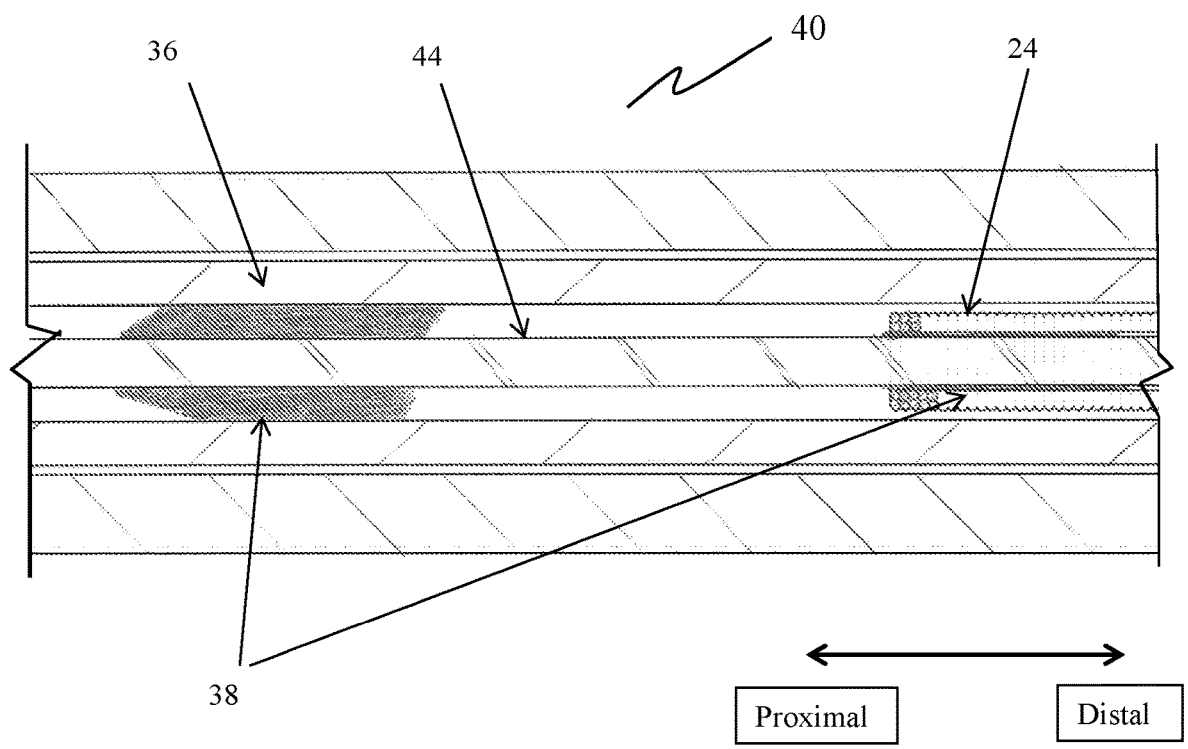
FIG. 4 illustrates a portion of an apparatus according to one or more aspects of the present disclosure.

FIG. 4 illustrates a cross-section of an apparatus 40 according to one or more aspects of the present disclosure. The apparatus 40 may be a catheter and may include an elongate member having a proximal portion and a distal portion. A rotatable drive cable may be disposed within the elongate member. FIG. 4 illustrates an indirect bond example, showing a portion of the imaging core that is adjacent to the optical connector where the drive cable 24 is inserted into the hypotube 36. The hypotube 36 may be fixedly attached to an optical connector (not shown) that may be positioned to the left side of the figure. The drive cable 24 and catheter may extend out from the right side of the figure. The optical fiber 44 may be bonded into the optical connector by adhesive, epoxy, or the like 38, and may extend within the drive cable 24 and catheter from the right side of the figure.

The apparatuses according to one or more aspects of the present application may implement a low-shear adhesive design that uses any low-shear strength material such as adhesive or epoxy that can be applied between the drive cable and hypotube. This type of material may shear when the applied torque exceeds a predetermined level.

The apparatuses according to one or more aspects of the present application may implement an optical fiber as a torque transmitter and fuse design that may utilize an optical fiber 44 to transmit torque to the drive cable 24. Any adhesive 38 may be used to attach optical fiber 44 to drive cable 24 to cause the optical fiber 44 to break under a predetermined torque level, preferably around approximately 0.09 mN-m. Torque strength of the optical fiber 44 may preferably be around 0.09 mN-m (or 0.90 Gram-centimeters). The low-shear adhesive 38 or optical fiber 44 may break away, functionally disconnecting the distal drive cable from the proximal motor drive unit in a range between around 0.01 mN-m and 0.50 mN-m torque force.

These design configurations necessarily involve no extra parts other than low-shear adhesive.

One or more aspects of the present disclosure may utilize small spot welds between the hypotube or torque shaft and the drive cable. These welds may break if the drive cable is subjected to torque in excess of a predetermined torque level.

Figure 5:
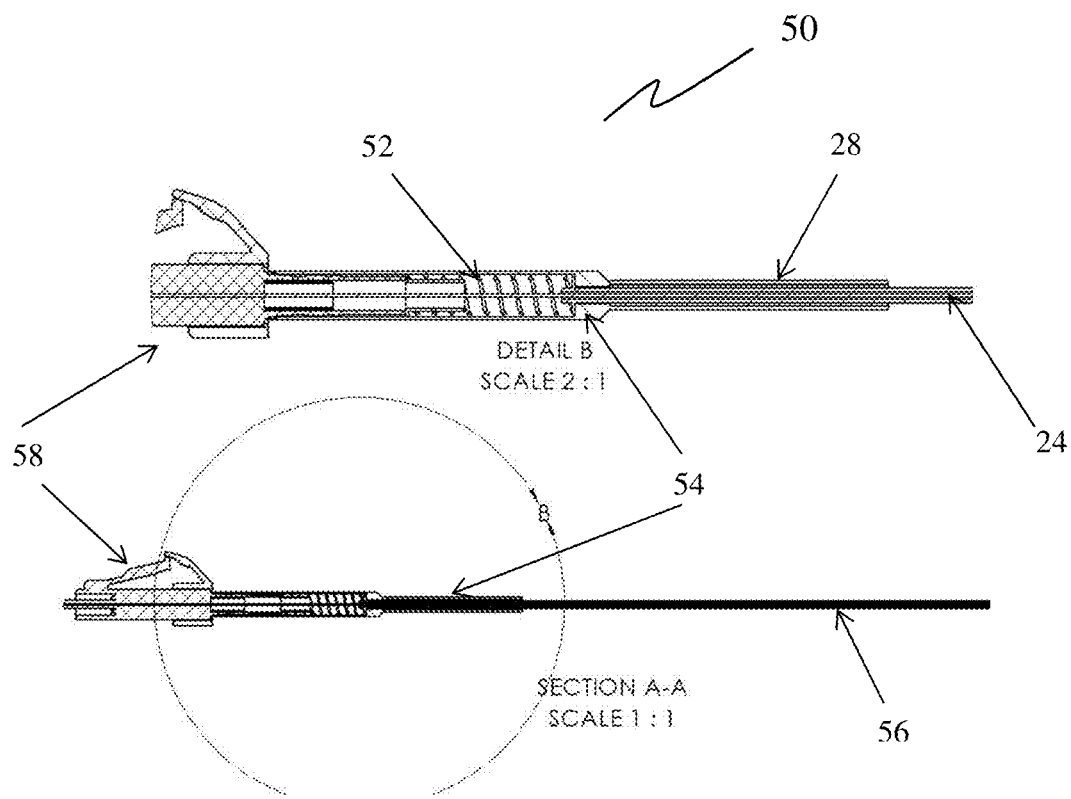
FIG. 5 illustrates a portion of an apparatus according to one or more aspects of the present disclosure.

FIGS. 5 through 8 show various views of another aspect of the present disclosure, and FIG. 5 illustrates a side-view cross-section of an apparatus 50 according to one or more aspects of the present disclosure. The apparatus 50 may be a catheter and includes a drive cable 24 having a proximal end and a distal end. A rotatable drive cable 24 is disposed within the catheter sheath 22 (not shown for clarity). In FIG. 5, a compression spring 52 applies a small force on the proximal end of the torque shaft 56 to keep the driving dog 62 engaged within cutout 64 of torque shaft 56 under normal working conditions. A driving dog adapter 54 may interconnect the adapter 54 with the drive cable 24 via torque shaft 56. The adapter 54 may be fitted to a fiber optic connector 58. A fiber optic 44 may be contained within the catheter sheath 22 (not shown)

The compression spring 52 may be housed inside the driving dog adapter 54 which may press onto the fiber optic connector 58 via interference fit for secure attachment and to retain concentricity. The torque shaft 56 may be slidably positioned inside the driving dog adapter 54 in concentric rotatable fashion, and whose rotation is driven by the driving dog adapter under normal operating conditions. A PTFE tube 28 may allow the torque shaft 56 to slide proximally to disengage the driving dog and may also permit torque shaft 56 to rotate freely in the event of a catheter complication that exerts excessive torque on the drive cable 24 beyond a predetermined level or when the imaging core cannot be advanced back to the starting position.

Since drill-through, disection and/or perforation can only happen with an applied force on the catheter in the distal direction, an equal and opposite force may be generated that is directed proximally on the rotating, imaging core and, in turn, the torque shaft 56. When sufficient excess torque or axial force in the proximal direction is applied, such as during catheter entanglement, kinked or prolapsed catheter sheath, the torque shaft may be forced proximally, disengaging the flange cutout from the driving dog and promptly stopping drive cable rotation.

Distinguishable configurational elements of this aspect of the present disclosure take advantage of the proximally directed force and driven motion toward the proximal end that occurs when the drive cable is pinched, such as when the catheter becomes entangled, and when the core cannot be advanced due to a compromised sheath. Since the outer wind of the drive cable may be the only portion of the drive cable that contacts the catheter sheath, and the outer wind may be a right-hand wind, the drive cable may tend to 'unscrew itself', that is to say, drive cable may try to back its way out of the catheter sheath when the sheath is pinched enough to pinch the drive cable. Should this complication occur, upon encountering the proximal force on the rotating drive cable, this embodiment quickly disengages the distal portion including the drive cable that is inside the anatomy from the motor drive unit outside the body, promptly stopping rotation of and/or withdrawing the drive cable and/or imaging core from the site of complication to reduce the chances of a drill-through and/or perforation.

Distinguishable configurational elements of this aspect of the present disclosure minimize risk of harm and provide additional failsafe and a layer of protection against the risk of harm to the patient, by causing rotation of the drive cable to stop or withdrawal of the drive cable based on sensing of excess torque and motor shut-off, or if the imaging core cannot advance due to a compromised sheath, or by causing shear failure in the event of torques encountered that are higher than a predetermined level.

Figure 6:
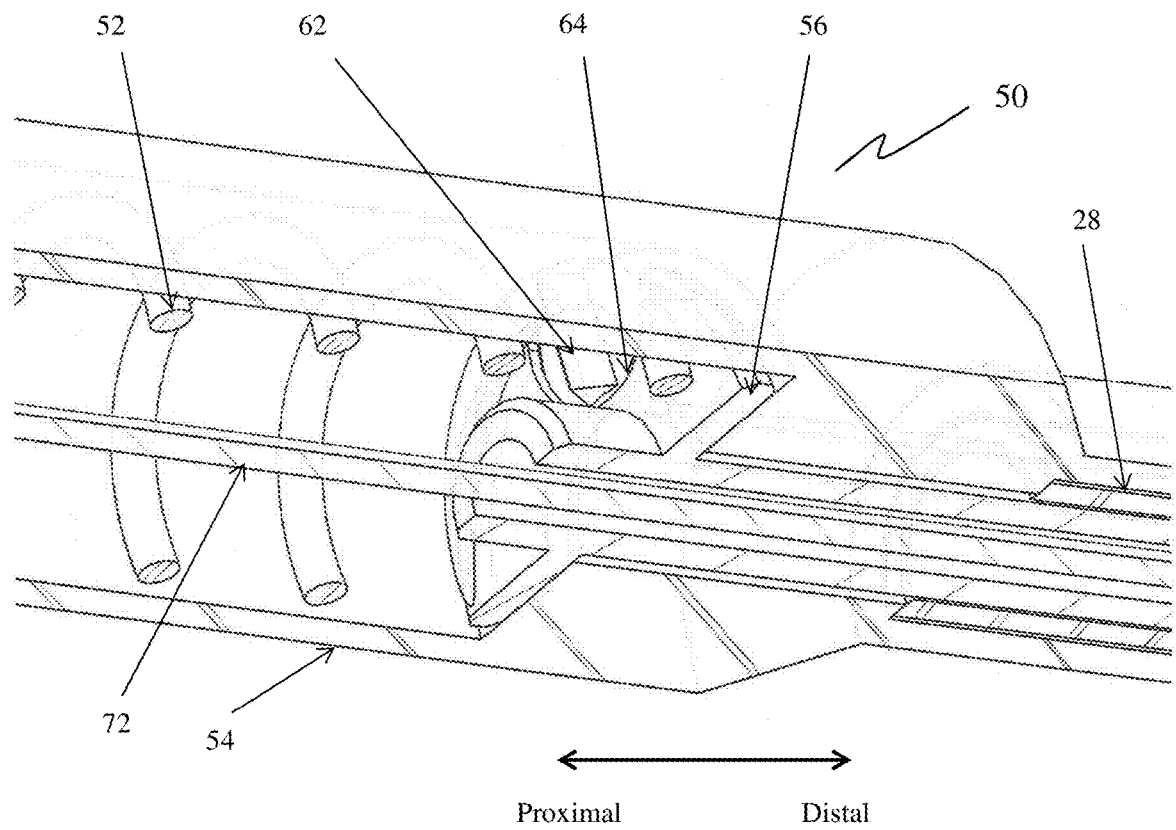
FIG. 6 illustrates a cross-sectional view of the apparatus of FIG. 5.

FIG. 6 illustrates a close-up, side view cross-section of the torque shaft 56 from driving dog adapter embodiment shown in FIG. 5 above of apparatus 50 according to one or more aspects of the present disclosure. The apparatus 50 may include a drive cable 24 (not shown) having a proximal end and a distal end. A rotatable drive cable 24 may be disposed within the catheter sheath (not shown for clarity). In FIG. 6, a driving dog 62 is illustrated in the flange cutout 64. The components, benefits and functions of this assembly are described above.

Figure 7:
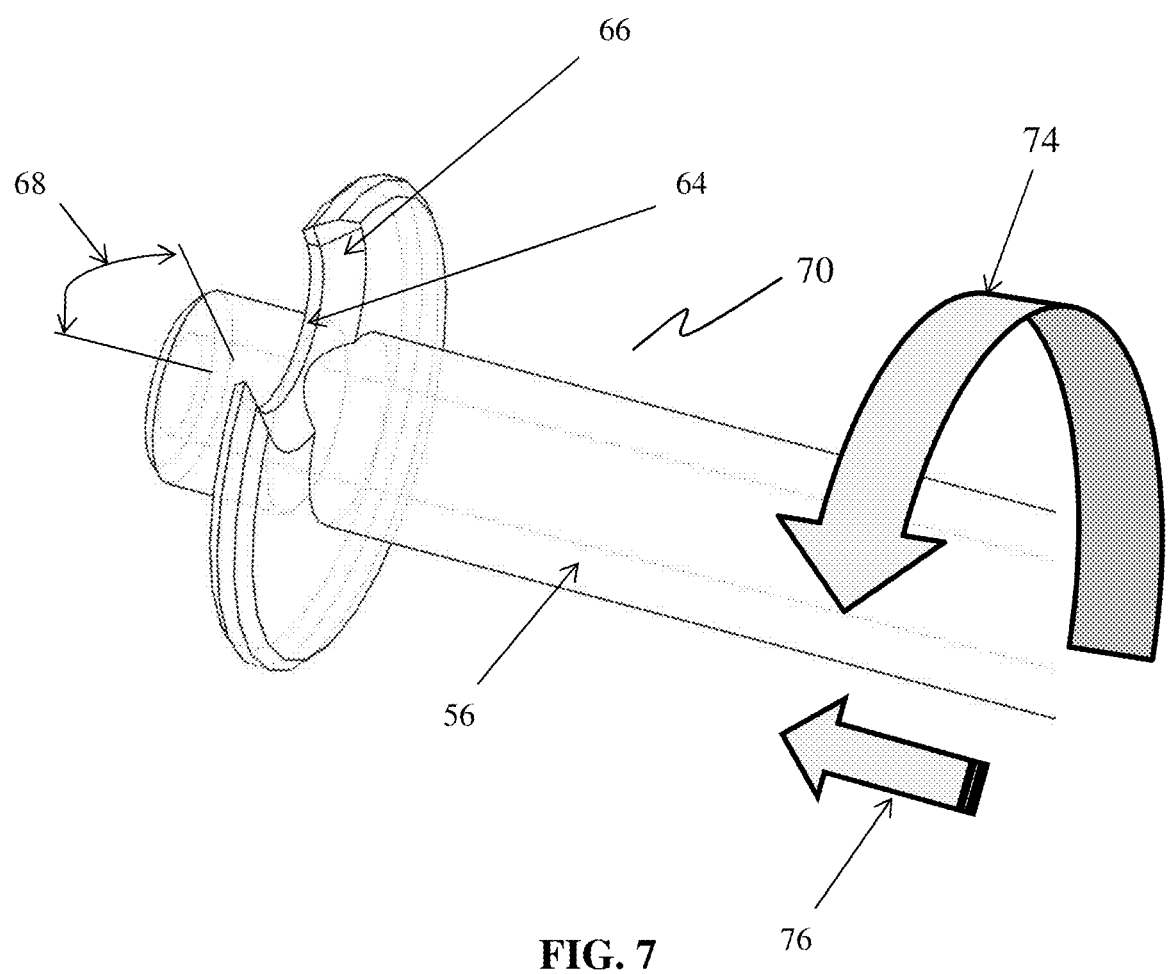
FIG. 7 illustrates an angled cutout edge of a cutout according to one or more aspects of the present disclosure.

FIG. 7 illustrates another close-up view of the torque shaft 56 of apparatus 70 according to one or more aspects of the present disclosure. The torque shaft 56 may include an angled cutout edge 66 that allows the driving dog 62 to disengage from the torque shaft cutout 64 under torque alone. A rotatable drive cable 24 may be disposed within and attached to the torque shaft 56 via adhesive. Angle 68 may be adjusted to disengage the driving dog from the torque shaft cutout 64 at a predetermined torque load 74, or via axial forces 76, which promptly stops rotation of the drive cable 24.

Figure 8:
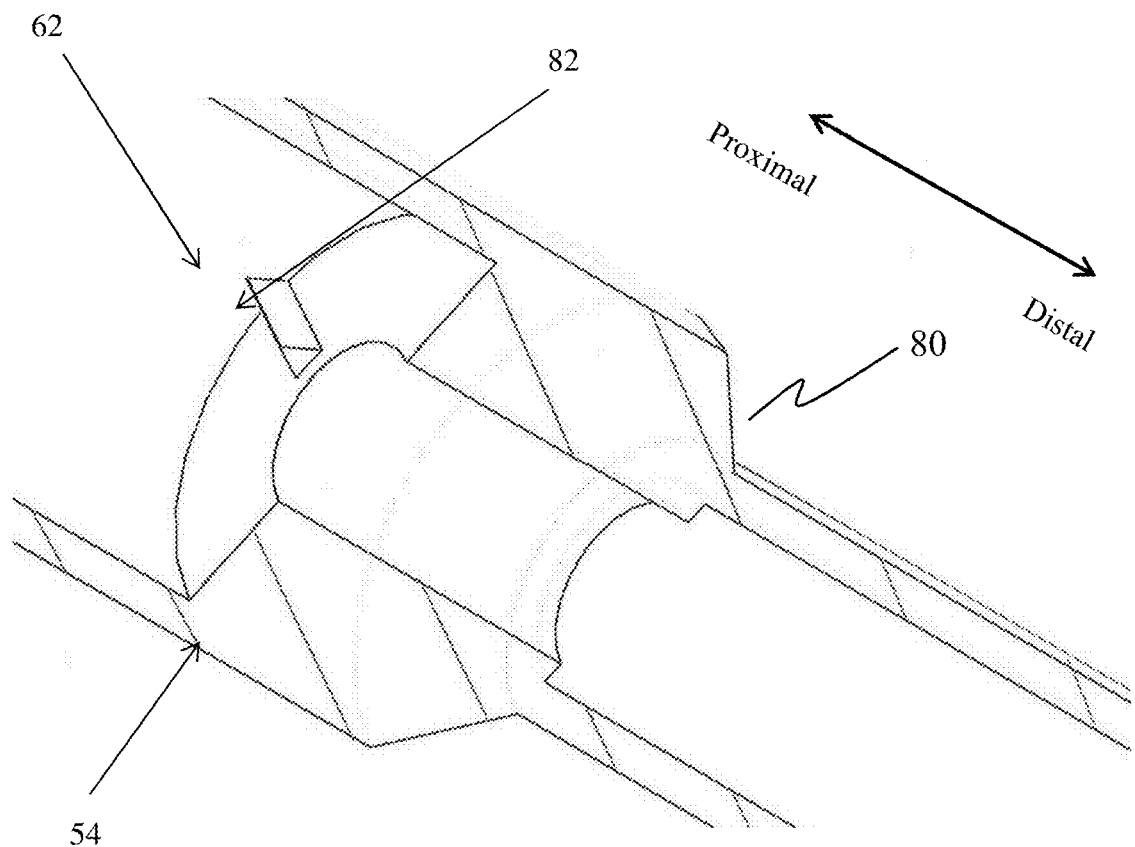
FIG. 8 illustrates an angled cutout edge of a cutout according to one or more aspects of the present disclosure.
Figure 10:
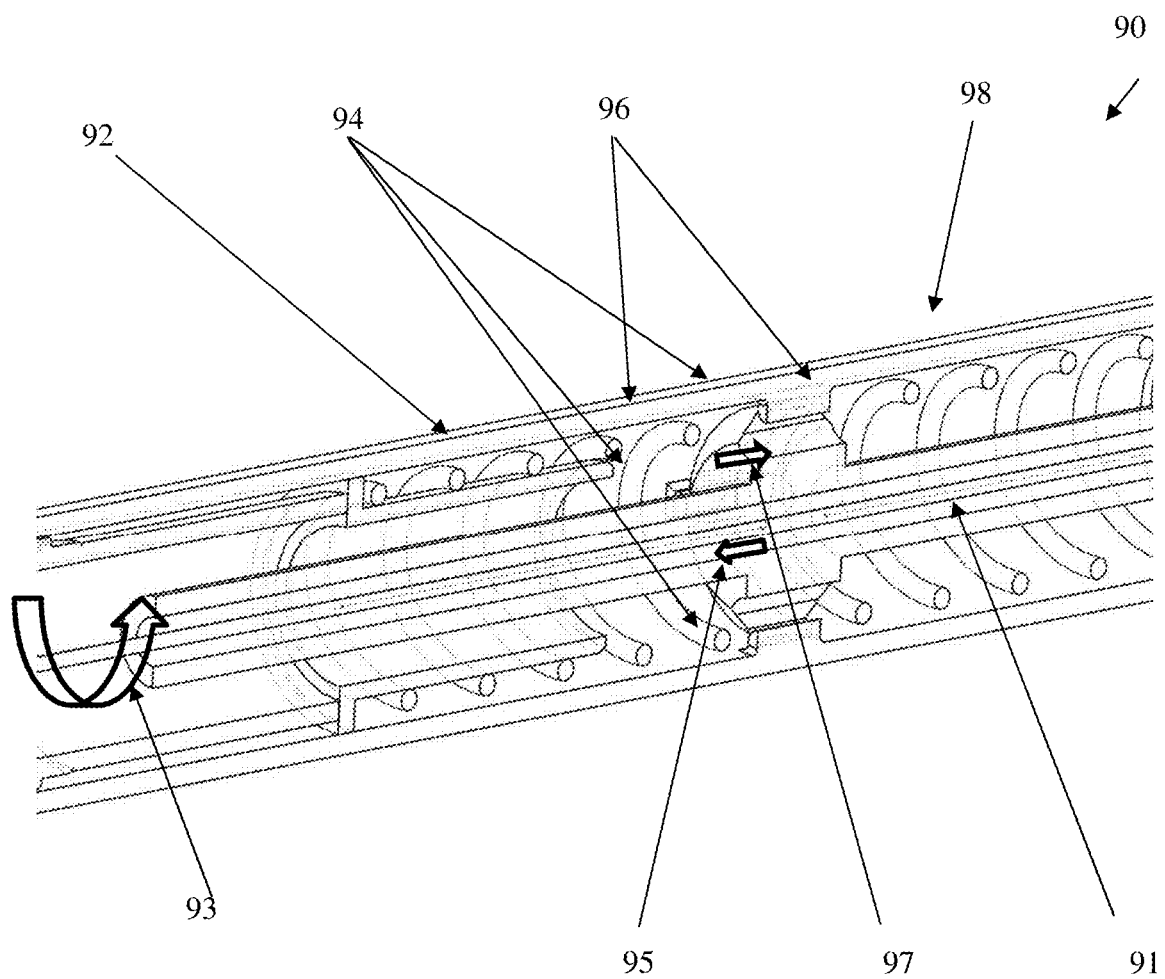

FIG. 8 illustrates a close-up, side-view cross-sectional view 80 of the driving dog adapter 54 according to one or more aspects of the present disclosure. The driving dog 62 may include an angled edge 82 of the driving dog 62. A rotatable drive cable may be disposed within the torque shaft 56. The components, benefits and functions of this assembly are described above.

Referring to FIG. 9(B), another embodiment of the present invention is shown in side-view cross-section and end-view cross-section (FIG. 9(A). This embodiment provides a mechanism to disengage the rotating mechanism, not shown for simplicity, from the drive cable that enters the anatomy. This entire segment of the system resides within the handle 26 of the device, and is designed such that failure always occurs outside of the anatomy, and thus protects the patient from the rotating components in the event of catheter entanglement or other dangerous failure within the anatomy. The hypotube 36 rotates within stationary pullback tube 28 and transmits torque from the rotating mechanism, such as a drive motor, to the drive cable 24, which rotates partially within the anatomy. The attachment between hypotube 36 and drive cable 24 comprises a mechanical crimp 84. Hypotube 36 is crimped onto drive cable 24 such that the cross-section of drive cable 24 is clamped by crimp 84, which provides adequate torque and tensile strength between hypotube 36 and drive cable 24 to operate under normal conditions. When either torque or tensile force exceeds a pre-determined limit, the drive cable 24 slips in the crimped hypotube 36, thus stopping the transfer of torque or tension from the rotating mechanism to the drive cable.

In one or more aspects according to the present disclosure, the device may include an operative element attached to the catheter handle 26. The operative element may be a transducer, such as an imaging and pressure sensor and/or device, or an optical element. The device may be a medical device, such as a catheter or the like. The mechanism may be a drive shaft, such as a wire-wound drive shaft or the like. The drive shaft may be interconnected with a motor drive device. The elongate member may include a catheter sheath assembly disposed about the drive cable in a concentric, telescoping assembly. The elongate member may be a sheath, and disengagement of the mechanism from the drive cable may be based on one or more of low-shear adhesive, broken optical fiber, an unsupported segment of the drive cable, slippage of crimped hypotube on drive cable and a driving dog structure.

Referring to FIG. to, a two-way driving dog adapter is shown in isometric side view cross-section. Similar to the driving dog adapter embodiment shown in FIGS. 5-8, this two-way adapter embodiment reacts to catheter complications within the anatomy during both pullback and re-advance core motion directions such as kinked, pinched or clamped catheter sheath that prevents the rotating, imaging core from translating normally. Should the sheath be kinked such that the imaging core cannot re-advance back to its distal starting position, rotary shaft 91 will be forced proximally per advance action 95, compressing advance spring 92 via advance action 95 when it encounters the kinked sheath during re-advancement to its start position because it is attached to the drive cable (not shown). This proximal force pushes the drive cable (not shown) and rotary shaft 91 per advance action 95, which compresses advance spring 92, disengaging rotary shaft 91 from outer housing dogs 94 from rotary shaft 91 and stopping rotation 93 immediately. Similarly, but acting in the opposite direction per pullback action 97, should the sheath get clamped or pinched such that the imaging core cannot move during an imaging pullback, the motor continues to pull the core proximally, which compresses pullback spring 96, disengaging rotary shaft 91 from dogs 94 and stopping rotation immediately.

Referring now to FIG. 11, the two-way driving dog adapter is shown in cross-section end view through the flange of rotary shaft 91, showing (4) driving dogs 94 and (4) corresponding cut-outs 99 in the flange of rotary shaft 91 which accept the driving dogs 94, providing rotation force to drive the imaging core during operation. Two-way drive dog adapter is located at the proximal end of imaging core, which comprises a proximal connector, hypotube adapter, hypotube, drive cable and distal optics housing (all not shown).

FIG. 12 is a flowchart illustrating a method according to one or more aspects of the present disclosure. In step S901, a catheter sheath is inserted into a subject, such as a patient or the like. The catheter sheath may be configured as described above and may be characterized as an elongate member having proximal and distal portions. A rotatable drive cable may be disposed within the elongate member. The drive cable may be connected to a mechanism to which torque can be applied, and being mechanically coupled to a control assembly. In step S902, torque is applied to the mechanism to drive the drive cable. In step S903, a determination is made as to whether the applied torque exceeds a predetermined level. If the applied torque does not exceed the predetermined level, the process returns to step S904 and continues to apply torque to rotate the imaging core to image the anatomy. On the other hand, if the applied torque does exceed the predetermined level, the process proceeds to either step S904 or step S905. In step S905, the mechanism is disengaged from the drive cable via sheared adhesive or broken optical fiber. Alternatively, in step S905, the drive cable is withdrawn from a site of complication that may occur. Should such a complication occur, upon encountering the proximal force on the rotating drive cable, this embodiment quickly disengages the distal portion including the drive cable that is inside the anatomy, promptly stopping rotation of and/or withdrawing the drive cable and/or imaging core from the site of complication to reduce the chances of a drill-through and/or perforation.

An operative element, such as a transducer or the like, may be mounted on the distal end of the drive shaft. The transducer may be an imaging device. The device may be a medical device, such as a catheter or the like. The drive cable may be a wire-wound drive cable. The drive cable may be interconnected with a motor drive device, and may further dispose a catheter sheath assembly about the drive cable in a concentric, telescoping assembly.

An exemplary system using the apparatus as described herein is an optical coherence tomography (OCT) system, as illustrated by FIG. 13. The OCT system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 114. In one or more embodiments, the system 100 may include a patient interface device or unit ("PIU") 110 and a catheter 112, where the catheter is the catheter descried in FIGS. 2-11, where the catheter is configured to disengage when the applied torque exceeds a predetermined level. The disengagement causes the rotational motion to stop or causes withdrawal.

The catheter 112 may interact with a sample 106, where the PIU engages with the user. In one or more embodiments, the system 100 includes an interferometer or an interferometer is defined by one or more components of the system 100, such as, but not limited to, at least the light source lot, the reference arm 102, the sample arm 103, the splitter 104 and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample 106. The reference beam optionally goes through the phase shift unit 114 (when included in a system, as shown in the system 100), and the reference beam is reflected from the reference mirror 105 in the reference arm 102 while the sample beam is reflected or scattered from a sample 106 through the PIU (patient interface unit) 110 and the catheter 112 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 116. In one or more embodiments, the light source 101 may be a radiation source or a broadband light source that radiates in a broad band of wavelengths (e.g., laser, an organic Light-Emitting Diode (OLED), a Light-Emitting Diode (LED), a halogen lamp, an incandescent lamp, supercontinuum light source pumped by a laser, and/or a fluorescent lamp). In one or more embodiments, a Fourier analyzer including software and electronics may be used to convert the electrical analog signals into an optical spectrum.

Embodiment(s) and/or aspect(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits or circuitry (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, firmware, hardware, other component, or the like (e.g., a central processing unit (CPU), a micro processing unit (MPU), or the like), and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. An apparatus comprising:
an elongate member having proximal and distal portions;
a rotatable drive cable disposed within the elongate member, the drive cable being connectable to a mechanism which applies torque; and
a control assembly mechanically coupled to the drive cable, and configured to disengage the mechanism from the drive cable when the applied torque exceeds a predetermined level,
wherein disengagement of the mechanism from the drive cable causes rotation of the drive cable to stop or withdrawal of the drive cable; and
a short linear segment where the drive cable passes through an unsupported gap within a predetermined length range so the drive cable can wind up in the unsupported gap and be withdrawn from a site of complication or entanglement.

2. The apparatus according to claim 1, wherein the drive cable is axially translatable in proximal and distal directions.

3. The apparatus according to claim 1, wherein shear failure occurs in a case where applied torque exceeds the predetermined level.

4. The apparatus according to claim 1, wherein the elongate member is a sheath, and disengagement of the mechanism from the drive cable is based on at least one of a low-shear adhesive, a broken optical fiber, a slippage of a mechanical crimp of a hypotube on the drive cable, and a driving dog structure.

5. The apparatus according to claim 4, wherein disengagement of the mechanism from the drive cable is based on a slippage of a mechanical crimp of hypotube onto the drive cable and the unsupported segment of the drive cable.

6. The apparatus according to claim 1, wherein the unsupported gap has a length in a range between around two and twenty times the drive cable diameter.

7. The apparatus according to claim 1, wherein the unsupported gap has a diameter in a range between around three and twenty times the drive cable diameter.

8. The apparatus according to claim 1, wherein the mechanism is a drive shaft, and the drive shaft is interconnected with a motor drive unit.

9. The apparatus according to claim 8, wherein the drive cable is connected at a proximal portion to the drive shaft with adhesive.

10. The apparatus according to claim 1, further comprising:
a torque sensor configured to detect applied torque and quickly shut off a motor when the torque sensor senses a torque higher than a pre-determined range.

11. The apparatus according to claim 1, wherein the elongate member comprises a catheter sheath assembly disposed about the drive cable.

12. The apparatus according to claim 11, wherein the catheter sheath assembly comprises:
a hypotube disposed about the drive cable; and
a handle disposed about the hypotube,
wherein the hypotube is adhesively bonded to an optical fiber, the optical fiber is bonded to the drive cable, and there is no direct bond between the drive cable and the hypotube,
wherein optical fiber torque failure occurs in a case where applied torque is greater than a predetermined level.

13. A method comprising:
inserting, into a subject, an elongate member having proximal and distal portions, and a rotatable drive cable disposed within the elongate member, the drive cable being connected to a mechanism to which torque can be applied, and being mechanically coupled to a control assembly; and
applying torque to the control assembly, wherein the mechanism will disengage from the drive cable when the applied torque exceeds a predetermined level, and
wherein disengagement of the mechanism from the drive cable causes rotation of the drive cable to stop or withdrawal of the drive cable;
wherein the drive cable winds up in an unsupported gap such that the drive cable is withdrawn from a site of complication or entanglement.

14. The method according to claim 13, further comprising:
detecting applied torque with a torque sensor, and quickly shutting off a motor when torque exceeding a pre-determined limit is sensed.

15. A system comprising:
an imaging device;
a display;
a controller; and
an apparatus comprising:
an elongate member having proximal and distal portions;
a rotatable drive cable disposed within the elongate member, the drive cable being connectable to a mechanism to which torque can be applied; and
a short linear segment where the drive cable passes through an unsupported gap within a predetermined length range; and
a control assembly mechanically coupled to the drive cable, and configured to disengage the mechanism from the drive cable when the applied torque exceeds a predetermined level,
wherein disengagement of the mechanism from the drive cable causes rotation of the drive cable to stop or withdrawal of the drive cable, and wherein the drive cable can wind up in the unsupported gap and be withdrawn from a site of complication or entanglement.

16. The system according to claim 15, wherein the elongate member is a sheath, and disengagement of the mechanism from the drive cable is based on at least one of a shear adhesive, a broken optical fiber, a slippage of a mechanical crimp of a hypotube on the drive cable, and a driving dog structure.

17. The system according to claim 15, further comprising a torque sensor configured to detect applied torque, and quickly shutting off a motor when the torque exceeds a pre-determined limit.

18. The system according to claim 15, wherein the mechanism is a drive shaft, and the drive shaft is interconnected with a motor drive unit.

* * * * *